(12) United States Patent
Kamikawa et al.

(10) Patent No.: US 8,491,726 B2
(45) Date of Patent: Jul. 23, 2013

(54) LIQUID PROCESSING APPARATUS AND PROCESS LIQUID SUPPLYING METHOD

(75) Inventors: Yuji Kamikawa, Koshi (JP); Shigenori Kitahara, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 773 days.

(21) Appl. No.: 12/232,458

(22) Filed: Sep. 17, 2008

(65) Prior Publication Data
US 2009/0078287 A1 Mar. 26, 2009

(30) Foreign Application Priority Data

Sep. 26, 2007 (JP) .................................. 2007-249371
Aug. 28, 2008 (JP) .................................. 2008-219340

(51) Int. Cl.
*B08B 3/00* (2006.01)
(52) U.S. Cl.
USPC ........ 134/56 R; 134/94.1; 134/95.1; 134/99.1
(58) Field of Classification Search
USPC ........... 134/18, 56 R, 94.1, 95.1, 99.1, 100.1, 134/113, 26, 34, 36, 42
See application file for complete search history.

(56) References Cited

U.S. PATENT DOCUMENTS

| | | | | |
|---|---|---|---|---|
| 5,439,569 A | * | 8/1995 | Carpio | 134/1.3 |
| 6,766,818 B2 | * | 7/2004 | Kashkoush et al. | 137/3 |
| 6,799,883 B1 | * | 10/2004 | Urquhart et al. | 366/152.4 |

FOREIGN PATENT DOCUMENTS

| | | |
|---|---|---|
| JP | 60-165560 | 8/1985 |
| JP | 62-8040 | 1/1987 |
| JP | 10-154683 | 6/1998 |
| JP | 2005-189207 | 7/2005 |

* cited by examiner

*Primary Examiner* — Eric Golightly
(74) *Attorney, Agent, or Firm* — Smith, Gambrell & Russell, LLP

(57) ABSTRACT

A liquid processing apparatus includes: a processing part 80 configured to process an object to be processed by a process liquid; a supply path 1 connected to the processing part 80, the supply path 1 being configured to guide the process liquid to the processing part 80; a solvent supply part 7 configured to supply a solvent to the supply path 1; and a chemical-liquid supply part 5 configured to supply a chemical liquid to the supply path 1 through a chemical-liquid supply path so as to generate a chemical liquid diluted with the solvent. A measuring part 10, which is configured to measure a conductivity of the chemical liquid diluted with the solvent, is disposed in the supply path at a position downstream from a connection points 25*a*, 35*a*, 45*a*, to which the chemical-liquid supply path 6 is connected. An additional chemical-liquid supply part 1, which is configured to supply an additional chemical liquid different from the chemical liquid through an additional chemical-liquid supply path 3, is connected to the supply path at a position downstream from a measuring point 10*a* on which the measuring part 10 is disposed.

4 Claims, 1 Drawing Sheet

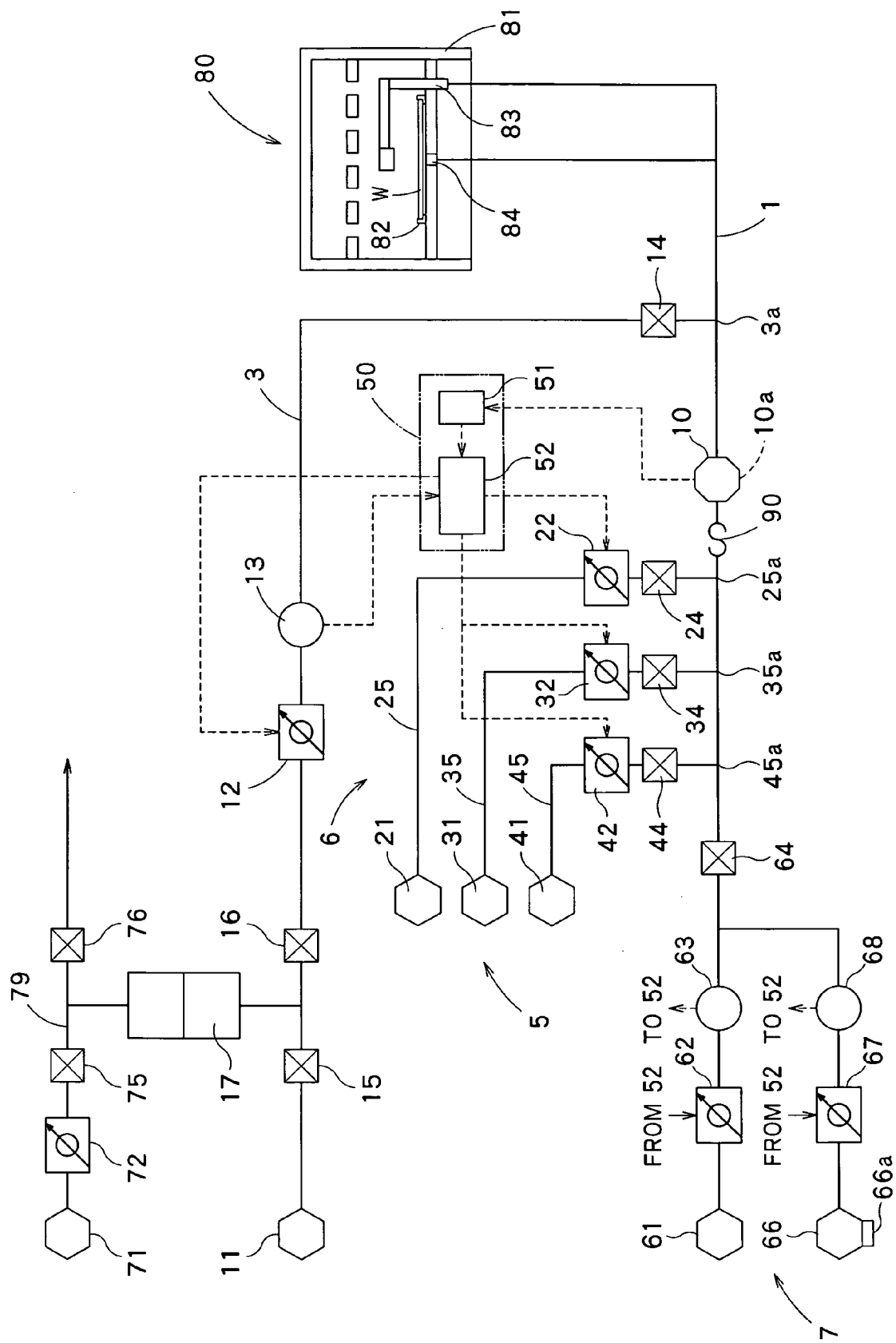

US 8,491,726 B2

LIQUID PROCESSING APPARATUS AND PROCESS LIQUID SUPPLYING METHOD

CROSS REFERENCE TO RELATED APPLICATIONS

This application is based upon and claims the benefit of priority from the prior Japanese Patent Application No. 2007-249371 filed on Sep. 26, 2007 and the prior Japanese Patent Application No. 2008-219340 filed on Aug. 28, 2008, the entire contents of which are incorporated herein by reference.

FIELD OF THE INVENTION

The present invention relates to a liquid processing apparatus configured to measure a concentration of a chemical liquid contained in a process liquid and then to process an object to be processed by means of the process liquid, and a process liquid supplying method for supplying a process liquid to an object to be processed.

BACKGROUND ART

When a semiconductor wafer (hereinafter also referred to as "wafer") as an object to be processed is washed, there have been conventionally used an ammonia peroxide mixture (SC1) made by adding $NH_4OH$ (ammonium hydroxide) and a hydrogen peroxide solution to a deionized water as a solvent, a hydrochloric acid-peroxide mixture (SC2) made by adding hydrochloric acid and a hydrogen peroxide solution to a deionized water as a solvent, and diluted hydrofluoric acid made by diluting hydrofluoric acid with a deionized water.

The ammonia peroxide mixture (SC1) is mainly used for removing particles adhering to a wafer, the hydrochloric acid-peroxide mixture is mainly used for removing metal contaminations from a wafer, and the diluted hydrofluoric acid is mainly used for removing contaminations from a wafer.

In order to measure concentrations of chemical liquids, such as the ammonia peroxide mixture (SC1), the hydrochloric acid-peroxide mixture (SC2), and the diluted hydrofluoric acid, which are contained in process liquids, there are known a method of measuring a conductivity of a process liquid, and a method of measuring a transmittance of light passing through a process liquid (absorbance of the process liquid) (see, JP62-8040A, JP10-154683A, and JP2005-189207A).

However, as described above, the ammonia peroxide mixture (SC1) contains two chemical liquids, i.e., $NH_4OH$ and a hydrogen peroxide solution. Similarly, the hydrochloric acid-peroxide mixture (SC2) contains two chemical liquids, i.e., hydrochloric acid and a hydrogen peroxide solution.

Thus, when a conductivity of a process liquid is measured so as to measure concentrations of the chemical liquids, since a conductive effect of one chemical liquid and a conductive effect of the other chemical liquid are mixed with each other, it is difficult to measure exact concentrations of the respective chemical liquids. Meanwhile, when a light transmittance (absorbance) of the process liquid is measured so as to measure concentrations of the chemical liquids, although concentrations of the respective chemical liquids can be exactly measured, a long period is required for the measurement.

When there is used a process liquid containing a chemical liquid of a relatively higher density, and thus a large amount of the chemical liquid is supplied, a concentration of the chemical liquid can be measured by directly measuring a flow rate of the chemical liquid to be supplied. However, when there is used a process liquid containing a chemical liquid of a relatively lower density, since an amount of the chemical liquid to be supplied is small, it is extremely difficult to exactly measure a flow rate of the chemical liquid which is being supplied.

DISCLOSURE OF THE INVENTION

The present invention has been made in view of the above circumstances. The object of the present invention is: to provide a liquid processing apparatus that is capable of, when a concentration of a process liquid containing two or more kinds of chemical liquids, promptly and exactly measuring concentrations of the chemical liquids, and is capable of, when a concentration of a process liquid containing a chemical liquid of relatively a lower concentration, exactly measuring a concentration of the chemical liquid; and to provide a process liquid supplying method for supplying a process liquid to an object to be processed.

A liquid processing apparatus according to the present invention is a liquid processing apparatus that processes an object to be processed by using a process liquid generated by mixing a solvent and a chemical liquid, the liquid processing apparatus comprising:

a processing part configured to process the object to be processed by the process liquid; a supply path connected to the processing part, the supply path being configured to guide the process liquid to the processing part; a solvent supply part configured to supply the solvent to the supply path; a chemical-liquid supply part configured to supply the chemical liquid to the supply path through a chemical-liquid supply path so as to generate a chemical liquid diluted with the solvent; a measuring part disposed in the supply path at a position downstream from a connection point to which the chemical-liquid supply path is connected, the measuring part being configured to measure a conductivity of the chemical liquid diluted with the solvent; and an additional chemical-liquid supply part connected to the supply path at a position downstream from a measuring point on which the measuring part is disposed, the additional chemical-liquid supply part being configured to supply an additional chemical liquid different from the chemical liquid through an additional chemical-liquid supply path.

In the above structure, the measuring part, which measures a conductivity, is disposed in the supply path at a position downstream from the connection point to which the chemical-liquid supply path is connected, and the additional chemical-liquid supply part, which supplies an additional chemical liquid different from the chemical liquid through the additional chemical-liquid supply path, is connected to the supply path at a position downstream from the measuring point on which the measuring part is disposed. Thus, when a concentration of a process liquid containing two or more kinds of chemical liquids, concentrations of the chemical liquids can be promptly and exactly measured. Further, even when a washing liquid contains a chemical liquid of a relatively lower density, and thus an amount of the chemical liquid to be supplied is small, an amount of the supplied chemical liquid can be exactly measured by the measuring part that measures a conductivity.

In the liquid processing apparatus according to the present invention, it is preferable that the additional chemical-liquid supply part supplies hydrogen peroxide as the additional chemical liquid.

The liquid processing apparatus according to the present invention preferably further comprises: a calculating part configured to calculate a concentration of the chemical liquid supplied from the chemical-liquid supply part, based on the conductivity measured by the measuring part; and an adjusting part configured to adjust an amount of the chemical liquid supplied from the chemical-liquid supply part, based on the concentration of the chemical liquid calculated by the calculating part.

Due to this structure, a concentration of the chemical liquid supplied from the chemical-liquid supply part can be adjusted at any given time, whereby the concentration of the chemical liquid can be rapidly varied to an appropriate concentration.

The liquid processing apparatus according to the present invention preferably further comprises: a concentration uniformity part disposed between the connection point to which the chemical-liquid supply path is connected and the measuring point on which the measuring part is disposed, configured to mix the solvent and the chemical liquid so as to make the solvent and the chemical liquid uniform.

Due to this structure, the measuring part can measure the conductivity of the chemical liquid diluted with the solvent accurately and output the measurement result of the conductivity of the chemical liquid diluted promptly.

In the liquid processing apparatus according to the present invention, it is preferable that the measuring part outputs the measurement result of the conductivity of the chemical liquid diluted with the solvent within 0.5 seconds after the chemical liquid diluted with the solvent passing the measuring part.

The liquid processing apparatus according to the present invention preferably further comprises: a solvent flowmeter disposed in the supply path, the solvent flowmeter being configured to measure a flow rate of the solvent flowing through the supply path; and an adjusting part configured to adjust an amount of the solvent supplied from the solvent supply part to the supply path, based on the flow rate of the solvent measured by the solvent flowmeter.

The liquid processing apparatus according to the present invention preferably further comprises: an additional chemical-liquid flowmeter disposed in the additional chemical-liquid supply path, the additional chemical-liquid flowmeter being configured to measure a flow rate of the additional chemical liquid flowing through the additional chemical-liquid supply path; and an adjusting part configured to adjust an amount of the additional chemical liquid supplied from the additional chemical-liquid supply part to the additional chemical-liquid supply path, based on the flow rate of the additional chemical liquid measured by the additional chemical-liquid flowmeter.

A process liquid supplying method according to the present invention is a process liquid supplying method for supplying a process liquid generated by mixing a solvent and a chemical liquid to an object to be processed, the process liquid supplying method comprising: a solvent supplying step in which the solvent is supplied to a supply path; a chemical-liquid supplying step in which the chemical liquid is supplied to the supply path so as to generate a chemical liquid diluted with the solvent; a measuring step in which a conductivity of the chemical liquid diluted with the solvent is measured so as to measure a concentration of the chemical liquid that has been supplied in the chemical-liquid supplying step; an additional chemical-liquid supplying step in which an additional chemical liquid different from the chemical liquid is supplied to the chemical liquid diluted with the solvent so as to generate the process liquid; and a substrate processing step in which the process liquid is supplied to the object to be processed.

In the above method, after a conductivity of the chemical liquid diluted with the solvent is measured so as to measure a concentration of the chemical liquid that has been supplied in the chemical-liquid supplying step, the additional chemical liquid is supplied to the chemical liquid diluted with the solvent so as to generate the process liquid. Thus, when a concentration of a process liquid containing two or more kinds of chemical liquids, concentrations of the chemical liquids can be promptly and exactly measured. Further, even when a washing liquid contains a chemical liquid of relatively a lower density, and thus an amount of the chemical liquid to be supplied is small, an amount of the supplied chemical liquid can be exactly measured by the measuring part that measures a conductivity.

In the process liquid supplying method according to the present invention, it is preferable that the additional chemical liquid supplied in the additional chemical-liquid supplying step is hydrogen peroxide.

The process liquid supplying method according to the present invention preferably further comprises: a calculating step in which a concentration of the chemical liquid that has been supplied in the chemical liquid supplying step is calculated, based on the conductivity that has been measured in the measuring step; and an adjusting step in which an amount of the chemical liquid to be supplied in the chemical-liquid supplying step is adjusted, based on the concentration of the chemical liquid calculated in the calculating step.

Due to this method, a concentration of the chemical liquid that is supplied in the chemical-liquid supplying step can be adjusted at any given time, whereby the concentration of the chemical liquid can be rapidly varied to an appropriate concentration.

The process liquid supplying method according to the present invention preferably further comprises: a uniformity step in which, between the chemical-liquid supplying step and the measuring step, the solvent and the chemical liquid are mixed so as to make the solvent and the chemical liquid uniform.

Due to this method, the conductivity of the chemical liquid diluted with the solvent are measured accurately and the measurement result of the conductivity of the chemical liquid diluted are output promptly.

In the process liquid supplying method according to the present invention, it is preferable that, in the measuring step, the measurement result of the conductivity of the chemical liquid diluted with the solvent are output within 0.5 seconds after the chemical liquid diluted with the solvent passing a measuring part.

The process liquid supplying method according to the present invention preferably further comprises: a solvent flow-rate measuring step in which a flow rate of the solvent flowing through the supply path is measured; and a solvent flow-rate adjusting step in which an amount of the solvent to be supplied in the solvent supplying step is adjusted, based on the flow rate of the solvent that has been measured in the solvent flow-rate measuring step.

The process liquid supplying method according to the present invention preferably further comprises an additional chemical-liquid flow-rate measuring step in which a flow rate of the additional chemical liquid that has been supplied in the additional chemical-liquid supplying step is measured; and an additional chemical-liquid flow-rate adjusting step in which an amount of the additional chemical liquid to be supplied in the additional chemical-liquid supplying step is adjusted, based on the flow rate of the additional chemical liquid that has been measured in the additional chemical-liquid flow-rate measuring step.

In the present invention, after a conductivity of the chemical liquid diluted with the solvent is measured, the additional chemical liquid different from the chemical liquid is supplied. Thus, when a concentration of a process liquid containing two or more kinds of chemical liquids, concentrations of the chemical liquids can be promptly and exactly measured. Further, even when a washing liquid contains a chemical liquid of relatively a lower density, and thus an amount of the chemical liquid to be supplied is small, an amount of the supplied chemical liquid can be exactly measured by the measuring part that measures a conductivity.

BRIEF DESCRIPTION OF THE DRAWINGS

FIG. 1 is a schematic structural view showing an embodiment of a liquid processing apparatus according to the present invention.

MODE FOR CARRYING OUT THE INVENTION

Embodiment

Embodiments of the liquid processing apparatus and the process liquid supplying method according to the present invention will be described herebelow with reference to the drawings. FIG. 1 is a schematic structural view showing an embodiment of the liquid processing apparatus according to the present invention.

The liquid processing apparatus in this embodiment is an apparatus for processing a semiconductor wafer (hereinafter also referred to as "wafer W") as an object to be processed, with the use of a process liquid that is generated by mixing a solvent and a chemical liquid.

As shown in FIG. 1, the liquid processing apparatus includes: a processing part 80 configured to process a wafer W by means of a process liquid; a supply path 1 connected to the processing part 80, the supply path 1 being configured to guide a process liquid to the processing part 80; a solvent supply part 7 configured to supply a solvent to the supply path 1; and a chemical-liquid supply part 5 configured to supply a chemical liquid to the supply path 1 through a chemical-liquid supply path 6.

The processing part 80 has: a casing 81; a holding part 82 disposed in the casing 81, the holding part 82 being configured to hold a wafer W; a process-liquid supply part 83 configured to supply a process liquid onto a front surface (upper surface) of the wafer W held by the holding part 82; and a rear process-liquid supply part 84 configured to supply a process liquid onto a rear surface (lower surface) of the wafer W.

As shown in FIG. 1, the chemical-liquid supply part 5 has: a hydrofluoric-acid supply part 21 configured to supply hydrofluoric acid; a hydrochloric-acid supply part 31 configured to supply hydrochloric acid; and an $NH_4OH$ supply part 41 configured to supply $NH_4OH$ (ammonium hydroxide).

As shown in FIG. 1, the chemical-liquid supply path 6 has: a hydrofluoric-acid supply path 25 configured to introduce the hydrofluoric acid supplied from the hydrofluoric-acid supply part 21 to the supply path 1; a hydrochloric-acid supply path 35 configured to introduce the hydrochloric acid supplied from the hydrochloric-acid supply part 31 to the supply path 1; and an $NH_4OH$ supply path 45 configured to introduce the $NH_4OH$ supplied from the $NH_4OH$ supply part 41.

As shown in FIG. 1, the hydrofluoric-acid supply path 25 connected to the hydrofluoric-acid supply part 21 is provided with a hydrofluoric-acid regulator 22 configured to regulate a flow rate of the hydrofluoric acid flowing through the hydrofluoric-acid supply path 25. Similarly, the hydrochloric-acid supply path 35 connected to the hydrochloric-acid supply part 31 is provided with a hydrochloric-acid regulator 32 configured to regulate a flow rate of the hydrochloric acid flowing through the hydrochloric-acid supply path 35, and the $NH_4OH$ supply path 45 connected to the $NH_4OH$ supply part 41 is provided with an $NH_4OH$ regulator 42 configured to regulate the $NH_4OH$ flowing through the $NH_4OH$ supply path 45.

As shown in FIG. 1, the hydrofluoric-acid supply path 25 is connected to the supply path 1 at a connection position 25a downstream from the hydrofluoric-acid regulator 22 via a hydrofluoric-acid supply valve 24 that can be opened and closed. Similarly, the hydrochloric-acid supply path 35 is connected to the supply path 1 at a connection position 35a downstream from the hydrochloric-acid regulator 32 via a hydrochloric-acid valve 34 that can be opened and closed, and the $NH_4OH$ supply path 45 is connected to the supply path 1 at a connection position 45a downstream the $NH_4OH$ regulator 42 via an $NH_4OH$ supply valve 44 that can be opened and closed.

As shown in FIG. 1, the solvent supply part 7 has: a DIW supply part 61 configured to supply a deionized water (DIW) to the supply path 1; and a heated DIW supply part 66 configured to supply a deionized water (DIW) heated by a heating part 66a to the supply path 1.

As shown in FIG. 1, provided on a downstream side of the DIW supply part 61 is a deionized-water regulator 62 configured to regulate a flow rate of the deionized water flowing through the supply path 1. Provided on the downstream side of the deionized-water regulator 62 is a deionized-water flowmeter (solvent flowmeter) 63 configured to measure a flow rate of the deionized water flowing through the supply path 1. Similarly, provided on the downstream side of the heated DIW supply part 66 is a heated deionized-water regulator 67 configured to regulate a flow rate of the heated deionized water flowing through the supply path 1, and provided on the downstream side of the heated deionized-water regulator 67 is a heated deionized-water flowmeter (solvent flowmeter) 68 configured to measure a flow rate of the heated deionized water flowing through the supply path 1. Further, on the downstream side of the deionized-water flowmeter 63 and the heated deionized-water flowmeter 68, there is provided a deionized-water supply valve 64 that can be opened and closed.

As shown in FIG. 1, the deionized-water flowmeter 63 is connected to an adjusting part 52 of a control part 50 which will be described below. The adjusting part 52 is connected to the deionized-water regulator 62. Similarly, the heated deionized-water flowmeter 68 is connected to the adjusting part 52 of the control part 50, and the adjusting part 52 is connected to the heated deionized-water regulator 67.

A measuring part 10 configured to measure a conductivity of a chemical liquid diluted with a deionized water as a solvent is disposed in the supply path 1 on a downstream side of the connection positions 25a, 35a, 45a to which the chemical-liquid supply path 6 (hydrofluoric-acid supply path 25, hydrochloric-acid supply path 35, and $NH_4OH$ supply path 45) is connected.

As shown in FIG. 1, connected to the measuring part 10 is a calculating part 51 configured to calculate a concentration of the chemical liquid supplied from the chemical-liquid supply part 5, based on the conductivity measured by the measuring part 10. In addition, connected to the calculating part 51 is the adjusting part 52 configured to adjust an amount of the chemical liquid supplied from the chemical-liquid supply part 5 (hydrofluoric-acid supply part 21, hydrochloric-acid supply part 31, and $NH_4OH$ supply part 41) by means of the regulator (hydrofluoric-acid regulator 22, hydrochloric-acid regulator 32, and $NH_4OH$ regulator 42), based on the concentration of the chemical liquid calculated by the calculating part 51. The calculating part 51 and the adjusting part 52 constitute the control part 50.

As shown in FIG. 1, a hydrogen-peroxide supply part (additional chemical-liquid supply part) 11 is connected to the supply path 1 at a connection point 3a which is located downstream from a measuring point 10a where the measuring part 10 is disposed. The hydrogen-peroxide supply part 11 is configured to supply hydrogen peroxide (additional chemical liquid) through an additional chemical-liquid supply path 3, the hydrogen peroxide being different from any of the chemical liquids supplied from the chemical-liquid supply part 5.

As shown in FIG. 1, the additional chemical-liquid supply path 3 is provided with a hydrogen-peroxide regulator 12 configured to regulate a flow rate of the hydrogen peroxide flowing through the additional chemical-liquid supply path 3. Further, provided on the downstream side of the hydrogen-peroxide regulator 12 is a hydrogen-peroxide flowmeter (additional chemical-liquid flowmeter) 13 configured to measure a flow rate of the hydrogen peroxide flowing through the additional chemical-liquid supply path 3. The hydrogen-peroxide flowmeter 13 is connected to the adjusting part 52 of the control part 50, and the hydrogen-peroxide regulator 12 is connected to the adjusting part 52.

As shown in FIG. 1, a hydrogen-peroxide storage tank 17 is connected to a position between the hydrogen-peroxide supply part 11 and the hydrogen-peroxide regulator 12. By opening a first hydrogen-peroxide supply valve 15 while closing a second hydrogen-peroxide supply valve 16, hydrogen peroxide can be supplied from the hydrogen-peroxide supply part 11 to the hydrogen-peroxide storage tank 17. On the other hand, by opening the second hydrogen-peroxide supply valve 16 while closing the first hydrogen-peroxide supply valve 15, the hydrogen peroxide solution stored in the hydrogen-peroxide storage tank 17 can be supplied to a substrate processing apparatus.

Connected through a nitrogen supply path 79 to the hydrogen-peroxide tank 17 is a nitrogen supply part 71 configured to apply a predetermined pressure to the hydrogen peroxide stored in the hydrogen-peroxide storage tank 17. A nitrogen regulator 72 configured to regulate an amount of the nitrogen supplied from the nitrogen supply part 71 is disposed in the nitrogen supply path 79 at a position between the nitrogen supply part 71 and the hydrogen-peroxide storage tank 17.

As shown in FIG. 1, on the downstream side of the nitrogen regulator 72, there are disposed a nitrogen supply valve 75 configured to supply nitrogen to the hydrogen-peroxide storage tank 17, and a nitrogen discharge valve 76 configured to discharge nitrogen outside. The nitrogen discharge valve 76 is communicated with an outlet (not shown) through which nitrogen goes outside.

When nitrogen is supplied to the hydrogen-peroxide storage tank 17 and the hydrogen peroxide in the hydrogen-peroxide storage tank 17 is supplied to the supply path 1, the nitrogen supply valve 75 is opened while the nitrogen discharge valve 76 is closed. At this time, the first hydrogen-peroxide supply valve 15 is being closed, while the second hydrogen-peroxide supply valve 16 and the hydrogen-peroxide supply valve 14 are being opened.

On the other hand, when the nitrogen is discharged from the hydrogen-peroxide storage tank 17 and hydrogen peroxide is supplied into the hydrogen-peroxide storage tank 17 from the additional chemical-liquid supply part 11, the nitrogen supply valve 75 is closed, while the nitrogen discharge valve 76 is opened. At this time, the first hydrogen-peroxide valve 15 is being opened, while the second hydrogen-peroxide supply valve 16 is being closed.

A concentration uniformity pipe (a concentration uniformity part) 90, such as static mixer, is disposed between the connection point 25a, 35a, 45a to which the chemical-liquid supply path 6 is connected and the measuring point 10a on which the measuring part 10 is disposed, and the concentration uniformity pipe 90 is configured to mix the solvent and the chemical liquid so as to make the solvent and the chemical liquid uniform.

Next, an operation of this embodiment as structured above is described.

In the first place, there is described a case in which $NH_4OH$, which has been diluted with a deionized water to have a relatively lower concentration (e.g., $NH_4OH$:deionized water=1:100), is used as a washing liquid.

At first, by opening the deionized-water supply valve 64, a deionized water as a solvent is supplied to the supply path 1 (solvent supplying step). At this time, a flow rate of the deionized water flowing through the supply path 1 is measured by the deionized-water flowmeter 63, and the flow rate of the deionized water flowing through the supply path 1 is regulated by the deionized-water regulator 62 in accordance with a command from the adjusting part 52 based on the measured flow rate of the deionized water. Similarly, a flow rate of the heated deionized water flowing through the supply path 1 is measured by the heated deionized-water flowmeter 68, and the flow rate of the heated deionized water flowing through the supply path 1 is regulated by the heated deionized-water regulator 67 in accordance with a command from the adjusting part 52 based on the measured flow rate of the heated deionized water, so as to adjust a temperature of the deionized water (mixture of the deionized water supplied from the DIW supply part 61 and the heated deionized water supplied from the heated DIW supply part) flowing through the supply path 1.

Then, by opening the $NH_4OH$ supply valve 44, $NH_4OH$ as a chemical liquid is supplied to the supply path 1 through the $NH_4OH$ supply path 45 (chemical-liquid supplying step).

Then, the $NH_4OH$ comes to the concentration uniformity pipe 90, such as static mixer, together with the deionized water, and then the deionized water and the $NH_4OH$ are mixed so as to make the deionized water and the $NH_4OH$ uniform (uniformity step).

Then, a conductivity of the $NH_4OH$ diluted with the deionized water is measured by the measuring part 10 (measuring step). As described above, the deionized water and the $NH_4OH$ are mixed by the concentration uniformity pipe 90 so as to make the deionized water and the $NH_4OH$ uniform, therefore the measuring part 10 can measure the conductivity of the chemical liquid diluted with the solvent accurately. Furthermore, because the deionized water and the $NH_4OH$ are mixed so as to make the deionized water and the $NH_4OH$ uniform, the measuring part 10 can output the measurement result of the conductivity of the chemical liquid diluted with the solvent promptly to the calculating part 51 described below. Preferably, the measuring part 10 outputs the measurement result of the conductivity of the chemical liquid diluted with the solvent within 0.5 seconds after the chemical liquid diluted with the solvent passing the measuring part 10.

Then, a concentration of the diluted $NH_4OH$ is calculated by the calculating part 51 of the control part 50, based on the conductivity measured by the measuring part 10. Thereafter, a concentration of the $NH_4OH$ supplied from the $NH_4OH$ supply part 41 is calculated by the calculating part 51, based on the calculated concentration of the diluted $NH_4OH$ and the flow rate of the deionized water obtained from the deionized-water flowmeter 63 and the heated deionized-water flowmeter 68 (calculating step).

In the above case in which NH₄OH, which has been diluted with a deionized water to have a lower concentration, is used as a washing liquid, an amount of the NH₄OH supplied from the NH₄OH supply part 41 is very small. Thus, even when a flowmeter is located in the supply path 45, it may be impossible to exactly measure a flow rate of the NH₄OH. As a result, an exact concentration of the NH₄OH diluted with a deionized water may not be known. On the other hand, according to this embodiment, a concentration of the chemical liquid (diluted NH₄OH) whose volume has been increased by diluting the NH₄OH with a deionized water is measured by using the measuring part 10 that measures a conductivity. Thus, even when an amount of NH₄OH supplied from the NH₄OH supply part 41 is very small, an amount of the NH₄OH that has been supplied from the NH₄OH supply part 41 can be exactly measured.

In addition, the measuring part 10 does not measure a light transmittance (absorbance) of the diluted NH₄OH, but measures a conductivity thereof. Thus, as compared with a case in which a light transmittance is measured, a concentration of the NH₄OH can be more promptly detected.

As has been described above, after the concentration of the NH₄OH supplied from the NH₄OH supply part 41 is calculated by the calculating part 51, the adjusting part 52 of the control part 50 adjusts the NH₄OH regulator 42 based on the calculated concentration of the NH₄OH. Thus, a concentration of the NH₄OH supplied from the NH₄OH supply part 41 to the supply path 1 can be adjusted at any given time, whereby the concentration of the NH₄OH can be rapidly varied to an appropriate concentration.

Subsequently, the NH₄OH diluted with the deionized water is supplied to the process-liquid supply part 83 and the rear process-liquid supply part 84 of the processing part 80 (substrate processing step). In this step, since the NH₄OH whose concentration has been adjusted to an appropriate concentration based on the exactly calculated NH₄OH concentration is supplied to a wafer W, the wafer W can be precisely processed.

(Process by Ammonia Peroxide Mixture (SC1))

Next, there is described a case in which a wafer W is washed by using, as a washing liquid, an ammonia peroxide mixture (SC1) containing NH₄OH of a relatively higher concentration (the ammonia peroxide mixture is generated by blending an ammonia water, a hydrogen peroxide solution, and a water at a ratio of 1:1:5 by volume, for example).

At first, by opening the deionized-water supply valve 64, a deionized water as a solvent is supplied to the supply path 1 (solvent supplying step). At this time, a flow rate of the deionized water flowing through the supply path 1 is measured by the deionized-water flowmeter 63 (solvent flow-rate measuring step), and the flow rate of the deionized water flowing through the supply path 1 is regulated by the deionized-water regulator 62 in accordance with a command from the adjusting part 52 based on the measured flow rate of the deionized water (solvent flow-rate adjusting step). Similarly, a flow rate of the heated deionized water flowing through the supply path 1 is measured by the heated deionized-water flowmeter 68, and the flow rate of the heated deionized water flowing through the supply path 1 is regulated by the heated deionized-water regulator 67 in accordance with command from the adjusting part 52 based on the measured flow rate of the heated deionized water, so as to adjust a temperature of the deionized water (mixture of the deionized water supplied from the DIW supply part 61 and the heated deionized water supplied from the heated DIW supply part) flowing through the supply path 1.

Then, by opening the NH₄OH supply valve 44, NH₄OH as a chemical liquid is supplied to the supply path 1 through the NH₄OH supply path 45 (chemical-liquid supplying step).

At this time, by opening the second hydrogen-peroxide supply valve 16 and the hydrogen-peroxide supply valve 14, the hydrogen peroxide solution stored in the hydrogen-peroxide storage tank 17 is supplied to the supply path 1 (additional chemical-liquid supplying step).

At this time, the nitrogen supply valve 75 is being opened while the nitrogen discharge valve 76 is being closed. By means of a pressure of a nitrogen gas supplied from the nitrogen supply part 71, a predetermined pressure is applied to the hydrogen peroxide stored in the hydrogen-peroxide storage tank 17. In this manner, a hydrogen peroxide solution is stored in the hydrogen-peroxide storage tank 17 of relatively a smaller volume, and the hydrogen peroxide solution is supplied by applying a pressure thereto by a nitrogen gas. Therefore, an amount of the hydrogen peroxide solution to be supplied can be easily adjusted.

Then, a conductivity of the NH₄OH diluted with the deionized water is measured by the measuring part 10 (measuring step). Then, a concentration of the diluted NH₄OH is calculated by the calculating part 51 of the control part 50, based on the conductivity measured by the measuring part 10. Thereafter, a concentration of the NH₄OH supplied from the NH₄OH supply part 41 is calculated by the calculating part 51, based on the calculated concentration of the diluted NH₄OH and the flow rate of the deionized water obtained from the deionized-water flowmeter 63 and the heated deionized-water flowmeter 68 (calculating step).

According to this embodiment, a conductivity of the NH₄OH supplied from the NH₄OH supply part 41 can be detected by the measuring part 10, without the presence of hydrogen peroxide. Thus, without being affected by a conductive effect produced by hydrogen peroxide, it is possible to measure a conductivity derived only from a conductive effect produced by the NH₄OH, so that a concentration of the NH₄OH can be exactly calculated.

In a conventional case in which a conductivity of a mixture of NH₄OH and hydrogen peroxide is measured, the smaller an amount of NH₄OH supplied from the NH₄OH supply part is, the more a conductive effect produced by the hydrogen peroxide contributes to the overall conductivity. Thus, as compared with the conventional method, the smaller an amount of NH₄OH supplied from the NH₄OH supply part is, the more the fact that a conductivity derived only from a conductive effect produced by the NH₄OH can be measured as this embodiment is advantageous.

In addition, the measuring part 10 does not measure a light transmittance (absorbance) of the diluted NH₄OH, but measures a conductivity thereof. Thus, as compared with a case in which a light transmittance is measured, a concentration of the NH₄OH can be more promptly detected.

As has been described above, after the concentration of the NH₄OH supplied from the NH₄OH supply part 41 is calculated by the calculating part 51, the adjusting part 52 of the control part 50 adjusts the NH₄OH regulator 42 based on the calculated concentration of the NH₄OH (adjusting step). Thus, a concentration of the NH₄OH supplied from the NH₄OH supply part 41 to the supply path 1 can be adjusted at any given time, whereby the concentration of NH₄OH can be rapidly varied to an appropriate concentration.

On the other hand, a flow rate of the hydrogen peroxide solution, which has been released from the hydrogen-peroxide storage tank 17 to flow through the hydrogen-peroxide supply path 3, is measured by the hydrogen-peroxide flowmeter 13 (additional chemical-liquid flow-rate measuring step), and a flow rate of the hydrogen peroxide solution is regulated by the hydrogen-peroxide regulator 12 in accordance with a command from the adjusting part 52 based on the measured flow rate of the hydrogen peroxide solution (additional chemical-liquid flow-rate adjusting step), during when a concentration of the diluted $NH_4OH$ is measured by the measuring part 10, and a concentration of the $NH_4OH$ supplied from the $NH_4OH$ supply part 41 is calculated by the calculating part 51, and then an amount of the supplied $NH_4OH$ is adjusted by the adjusting part 52.

Then, the hydrogen peroxide solution whose flow rate has been regulated as described above is mixed to the $NH_4OH$ that has been diluted to have an appropriate concentration as described above, so that an ammonia peroxide mixture (SC1) as a process liquid is generated in the supply path 1.

Subsequently, the ammonia peroxide mixture (SC1) is supplied to the process-liquid supply part 83 and the rear process-liquid supply part 84 of the processing part 80 (substrate processing step). In this step, since the ammonia peroxide mixture (SC1) whose concentration has been adjusted to an appropriate concentration based on the exactly calculated $NH_4OH$ concentration is supplied to a wafer W, the wafer W can be precisely processed.

That is to say, in addition to a case in which an amount of $NH_4OH$ supplied from the $NH_4OH$ supply part 41 is very small, which is the case as has been described above, in a case in which $NH_4OH$, hydrogen peroxide, and a deionized water are mixed, i.e., relatively larger amounts of the chemical liquids are supplied, a process-liquid concentration can also be exactly measured.

(Process by Hydrochloric Acid-Peroxide Mixture (SC2))

A washing process of a wafer W by using a hydrochloric acid-peroxide mixture (SC2) as a process liquid is substantially the same as the aforementioned process performed by using an ammonia peroxide mixture. Namely, the hydrochloric-acid supply valve 34, in place of the $NH_4OH$ supply valve 44, is opened and closed in this process, and other steps are substantially the same as those of the process performed by using an ammonia peroxide mixture (SC1). Thus, a detailed description is omitted.

According to this embodiment, even when hydrochloric acid which has been diluted to have a relatively lower concentration is used as a washing liquid, and thus an amount of hydrochloric acid supplied from the hydrochloric-acid supply part 31 is very small, a concentration of the chemical liquid (diluted hydrochloric acid) whose volume has been increased by the dilution can be measured by using the measuring part 10 that measures a conductivity. Thus, an amount of the hydrochloric acid supplied from the hydrochloric-acid supply part 31 can be exactly measured.

Even when a wafer W is washed by using a hydrochloric acid-peroxide mixture (SC2), a conductivity of the hydrochloric acid supplied from the hydrochloric-acid supply part 31 can be detected, without the presence of hydrogen peroxide. Thus, without being affected by a conductive effect produced by the hydrogen peroxide, it is possible to detect a conductivity derived only from a conductive effect produced by the hydrochloric acid, so that a concentration of the hydrochloric acid can be exactly calculated. Consequently, an exact amount of hydrochloric acid can be supplied to the processing part 80, whereby a wafer W can be processed by means of a hydrochloric acid-peroxide mixture (SC2) of an exact hydrochloric-acid concentration.

In addition, the measuring part 10 does not measure a light transmittance (absorbance) of the diluted hydrochloric acid), but measures a conductivity thereof. Thus, as compared with a case in which a light transmittance is measured, a concentration of the hydrochloric acid can be more promptly detected.

(Process by Diluted Hydrofluoric Acid)

Excluding that a hydrogen peroxide solution is not used, a washing process of a wafer W by using diluted hydrofluoric acid as a process liquid is also substantially the same as the aforementioned process performed by using an ammonia peroxide mixture (SC1). Namely, the hydrofluoric-acid supply valve 24, in place of the $NH_4OH$ supply valve 44 and the hydrogen-peroxide supply valve 14, is opened and closed in this process, and other steps are substantially the same as those of the process performed by using an ammonia peroxide mixture (SC1). Thus, a detailed description thereof is omitted.

When a wafer W is washed by using diluted hydrofluoric acid, since there is not used a hydrogen peroxide solution which is an additional chemical liquid, diluted hydrofluoric acid diluted with a deionized water serves as a process liquid.

The invention claimed is:

1. A liquid processing apparatus that processes an object to be processed by using a process liquid generated by mixing a solvent and a chemical liquid, the liquid processing apparatus comprising:

a processing part configured to process the object to be processed by the process liquid;

a supply path connected to the processing part, the supply path being configured to guide the process liquid to the processing part;

a solvent supply part configured to supply the solvent to the supply path;

a chemical-liquid supply part configured to supply the chemical liquid to the supply path through a chemical-liquid supply path so as to generate a chemical liquid diluted with the solvent;

a measuring part disposed in the supply path at a position downstream from a connection point to which the chemical-liquid supply path is connected, the measuring part being configured to measure a conductivity of the chemical liquid diluted with the solvent;

an additional chemical-liquid supply part connected to the supply path at a position downstream from a measuring point on which the measuring part is disposed, the additional chemical-liquid supply part being configured to supply an additional chemical liquid different from the chemical liquid to the chemical liquid diluted with the solvent through an additional chemical-liquid supply path;

a solvent flowmeter disposed in the supply path at a position upstream from the connection point, the solvent flowmeter being configured to measure only a flow rate of the solvent flowing through the supply path;

an additional chemical-liquid flowmeter disposed in the additional chemical-liquid supply path, the additional chemical-liquid flowmeter being configured to measure only a flow rate of the additional chemical liquid flowing through the additional chemical-liquid supply path;

a solvent regulator disposed in the supply path at a position upstream from the connection point, the solvent regulator adjusting only an amount of the solvent;

a chemical-liquid regulator disposed in the chemical-liquid supply path, the chemical liquid regulator adjusting only an amount of the chemical liquid;

an additional chemical-liquid regulator disposed in the additional chemical-liquid supply path, the additional chemical-liquid regulator adjusting only an amount of the additional chemical liquid; and an adjusting part configured to adjust an amount of the chemical liquid supplied from the chemical-liquid supply part by means of the chemical-liquid regulator, based on the conductivity measured by the measuring part, configured to adjust an amount of the solvent supplied from the solvent supply part to the supply path by means of the solvent regulator, based on the flow rate of the solvent measured by the solvent flowmeter, and configured to adjust an amount of the additional chemical liquid supplied from the additional chemical-liquid supply part to the additional chemical-liquid supply path by means of the additional chemical-liquid regulator, based on the flow rate of the additional chemical liquid measured by the additional chemical-liquid flowmeter.

2. The liquid processing apparatus according to claim 1, wherein the additional chemical-liquid supply part supplies hydrogen peroxide as the additional chemical liquid.

3. The liquid processing apparatus according to claim 1, further comprising:
   a concentration uniformity part disposed between the connection point to which the chemical-liquid supply path is connected and the measuring point on which the measuring part is disposed, configured to mix the solvent and the chemical liquid so as to make the solvent and the chemical liquid uniform.

4. The liquid processing apparatus according to claim 1, the measuring part outputs the measurement result of the conductivity of the chemical liquid diluted with the solvent within 0.5 seconds after the chemical liquid diluted with the solvent passes the measuring part.

* * * * *